United States Patent
Yamazaki et al.

[11] Patent Number: 5,508,369
[45] Date of Patent: Apr. 16, 1996

[54] ORGANOPOLYSILOXANES HAVING A SILANOL GROUP AND PROCESS OF MAKING THEM

[75] Inventors: Toshio Yamazaki; Nobuyuki Suzuki; Shinichi Morioka, all of Annaka; Shoji Ichinohe, Takasaki, all of Japan

[73] Assignee: Shin-Etsu Chemical Co., Ltd., Tokyo, Japan

[21] Appl. No.: 291,066

[22] Filed: Aug. 17, 1994

[30] Foreign Application Priority Data

Aug. 18, 1993 [JP] Japan ................................ 5-226438

[51] Int. Cl.⁶ .................................................. C08G 77/16
[52] U.S. Cl. .................. 528/32; 528/42; 528/10; 528/34; 556/454; 556/455; 556/456; 556/459
[58] Field of Search .................. 556/454, 455, 556/456, 459; 528/42, 32, 10, 34

[56] References Cited

U.S. PATENT DOCUMENTS

| | | | |
|---|---|---|---|
| 3,179,678 | 4/1965 | Daughenbaugh | 556/459 |
| 3,328,448 | 6/1967 | Barnes | 556/459 |
| 4,855,472 | 8/1989 | Burkhardt | 556/459 |
| 5,194,649 | 3/1993 | Okawa | 556/451 |

FOREIGN PATENT DOCUMENTS

544257A2   6/1993   European Pat. Off. .

*Primary Examiner*—John C. Bleutge
*Assistant Examiner*—Margaret Glass
*Attorney, Agent, or Firm*—Millen, White, Zelano & Branigan

[57] ABSTRACT

Novel organopolysiloxanes having one silanol group within a molecule and the method for manufacturing them at high purity and high yield. The organopolysiloxanes having a silanol group are expressed by the formula (1) below:

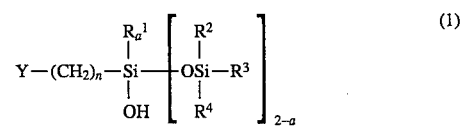

wherein $R^1$ is a monovalent hydrocarbon group with 1 to 8 carbon atoms, each of $R^2$, $R^3$ and $R^4$ is a monovalent hydrocarbon group with 1 to 8 carbon atoms or a siloxyl group expressed by $-OSiR^5R^7$, wherein $R^5$, $R^6$ and $R^7$ are monovalent hydrocarbon groups with 1 to 8 carbon atoms, Y is either a hydrogen atom, a halogen atom, or a monovalent hydrocarbon group with 1 to 12 carbon atoms, n is an integer of from 0 to 12, and a is either 0 or 1, with the proviso that the grouping $Y-(CH_2)_n-Si$ does not includes $H-Si$, $CH_3-Si$ or a hydrolyzable silyl group.

10 Claims, 6 Drawing Sheets

ORGANOPOLYSILOXANES HAVING A SILANOL GROUP AND PROCESS OF MAKING THEM

This invention relates to organopolysiloxanes having a silanol group and a process of making them, particularly to novel organopolysiloxanes having one silanol group within the molecule and the process of making them at high purity and high yield.

BACKGROUND OF THE INVENTION

Organopolysiloxanes having silanol groups at both molecular terminals, expressed by the chemical formula below, are conventionally known:

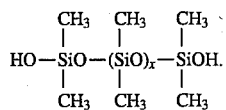

These compound are widely employed in many fields, for example, as a room temperature curable liquid silicone rubber.

Further, silanols expressed by the chemical formulae below are known as compounds having one silanol group in a molecule:

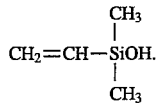

However, these silanols undergo a condensation through the mechanism (A) shown below and, as a result, high purity organopolysiloxanes may be obtained by distillation but only at a disadvantageously low yield:

On the other hand, an organopolysiloxane containing one silanol group at one molecular end, expressed as below, is of interest:

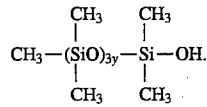

This compound may be synthesized by the living polymerization of cyclic organopolysiloxanes with silanols, as shown by the formula below, which is described in, for example, European Patent Specification, EP-A-0508490.

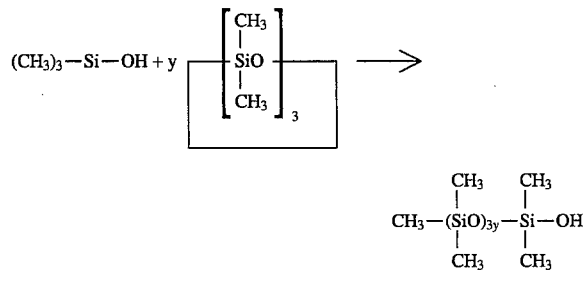

However, a complicated process is required to prepare such a silanol terminated compound with a high precision by this method and it also requires a high degree of technology. In addition, the importance of compounds having one silanol group per molecule has recently been recognized, therefore the development of methods which enable one to prepare them easily at high purity and high yield is strongly in demand.

SUMMARY OF THE INVENTION

The inventors investigated the high selectivity of a hydrogen halide elimination reaction between organohalosilanes and silanols, and discovered that compounds having one silanol group per molecule may be readily prepared at high purity and high yield through such reaction.

Therefore, a purpose of this invention is to provide novel organopolysiloxanes having one silanol group per molecule. Another purpose of this invention is to provide a more simple and advantageous manufacturing process for said organopolysiloxanes having a silanol group, resulting in high purity and high yield.

The purposes of this invention are achieved by the organopolysiloxanes having a silanol group, expressed by the formula (I) below, and the manufacturing method thereof:

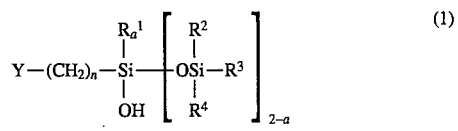

wherein $R^1$ is a substituted or unsubstituted monovalent hydrocarbon group of 1 to 8 carbon atoms, each of $R^2$, $R^3$, and $R^4$ is independently either a substituted or unsubstituted monovalent hydrocarbon group of 1–8 carbon atoms or a siloxyl group of the formula —$OSiR^5R^6R^7$, wherein $R^5$, $R^6$, and $R^7$ are substituted or unsubstituted monovalent hydrocarbon groups with 1 to 8 carbon atoms, Y is either a hydrogen atom, a halogen atom, or a monovalent organic group with 1 to 12 carbon atoms, n is an integer of from 0 to 12, preferably n is from 0 to 3, and a is either 0 or 1. However, the group, Y—$(CH_2)_n$—Si, does not include H-Si, $CH_3$-Si or hydrolyzable silyl groups.

Examples of hydrocarbon groups with 1 to 8 carbon atoms for $R^1$, $R^2$, $R^3$, $R^4$, $R^5$, $R^6$, and $R^7$ are: alkyl groups such as a methyl group, an ethyl group, a propyl group, and a butyl group; cycloalkyl groups such as a cyclopentyl group and a cyclohexyl group; aryl groups such as a phenyl group; aralkyl groups such as a benzyl group; alkenyl groups such as a vinyl group, and an allyl group; and hydrocarbon groups substituted with halogens or cyano, such as a chloromethyl group, a 3,3,3-trifluoropropyl group, and a 2-cyanoethyl group.

Examples of siloxyl groups expressed by —$OSiR^5R^6R^7$ in $R^2$, $R^3$, and $R^4$ are a trimethyl siloxyl group, an ethyl dimethyl siloxyl group, a 3,3,3-trifluoropropyl dimethyl siloxyl group, and a 2-cyanoethyl dimethyl siloxyl group. Each of $R^1$, $R^2$, $R^3$, $R^4$, $R^5$, $R^6$, and $R^7$ may be the same or different, however, they are desirably methyl groups due to the ease in synthesis.

Further, Y is either a hydrogen atom, a halogen atom, or a monovalent organic group with 1 to 12 carbon atoms, and it may be appropriately selected depending upon the characteristics desired for the organopolysiloxane having a silanol group of this invention. For example, when Y is a hydrogen atom or a halogen atom, the organopolysiloxane will contain a linear alkyl group or a halogen substituted linear alkyl group, respectively.

particular examples of Y as a monovalent organic group with 1 to 12 numbers of carbon atoms are: the saturated hydrocarbon groups such as linear alkyls, branched alkyls, and cyclic alkyls; the unsaturated hydrocarbon groups such as alkenyl groups and alkynyl groups; and the aromatic hydrocarbon groups such as a phenyl group and a naphthyl group. Further, a part, or all, of the hydrogen atoms in these organic groups may be substituted by halogen atoms, (meth) acryloyl groups, cyano groups, and nitro groups, or Y, as a whole, may be one of these groups. Also, the organic groups may also contain hetero atoms such as nitrogen, oxygen and sulfur, e.g., as amine, amide, hydroxy, ether, thiol or thioether groups.

However, Y must be stable when in the form of an organohalosilane, expressed by the formula below, from the performance view point during the manufacturing method of this invention:

$$Y-(CH_2)_n-\underset{\underset{X_{3-a}}{|}}{\overset{\overset{R^1_a}{|}}{Si}}$$

wherein X, $R^1$, Y, n and a are the same as described in formula (1).

Considering this point, a monovalent organic group Y is preferably either a (meth) acryloyl group, a vinyl group, a halogen substituted hydrocarbon group or a cyano group. Among the halogen substituted hydrocarbon groups, perfluoroalkyl groups such as a trifluoromethyl group, a nonafluorobutyl group, and a heptadecafluorooctyl groups are particularly preferred.

The organopolysiloxane having a silanol group of this invention is prepared by the following synthetic reactions, expressed by the equations (B) and (C).

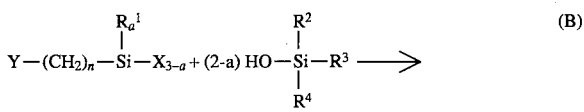

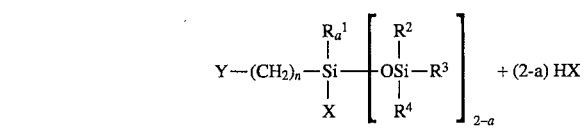

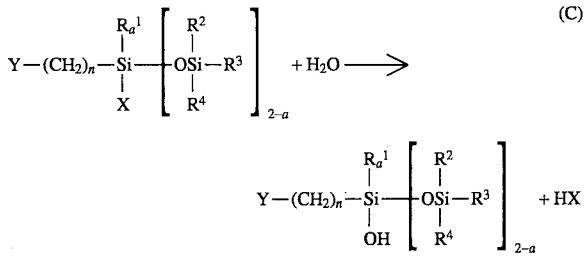

therein the variables are as defined above.

In the reaction (B), the elimination of hydrogen halide takes place between organohalosilane expressed by the formula (2) and the silanols expressed by the formula (3) in order to prepare a monohalo-polysiloxane. Then the monohalo-polysiloxane is hydrolyzed by the reaction (C) to obtain the organopolysiloxane having a silanol group, expressed by formula (1), of this invention.

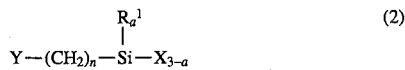

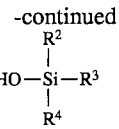

The synthesis of the compound expressed by the formula (1) from the compounds expressed by the formulae (2) and (3) is new. However, the elementary reactions (B), dehydrohalogenation, and (C), hydrolysis, are already well-known in general. Therefore, utilization of solvents, catalysts, agents for the hydrogen halide elimination, and stabilizers, and the reaction conditions such as reaction temperature, reaction time, and purification methods would have been known to one of ordinary skill in the art, and are not particularly limited to specifics during the performance of these reactions.

The selectivity in the elimination of the hydrogen halide in reaction (B) is high, and the reactivity of the Si-X bond in the compound (2) reduces as the reaction proceeds due to the effect of the increased stearic hindrance at the vicinity of the Si-X bond by addition of the triorganosiloxy groups. Therefore, if the progress of the hydrogen halide elimination is expressed by the compound expressed by the formula (4), the rate of the reaction between the Si-X bond in the formula (4) and the compound (3) is in the order of (b=3)<(b=2)<<(b=1):

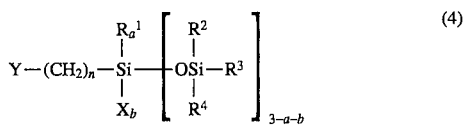

wherein X $R^1$, $R^2$, $R^3$, $R^4$, Y, n, and a are the same as described in the chemical formula (I) and b is either 1, 2, or 3, and a+b≦3.

Considering the above, it was discovered that controlling the molar ratio of the compounds of the formulae (2) and (3), respectively, to be substantially at 1/(2-a) or about 1/(2-a) result in selectivity to the intended product of the compound (1).

When this molar ratio is significantly smaller than 1/(2-a), the completely triorganosiloxyl substituted product, expressed by the formula (5) will be more readily produced:

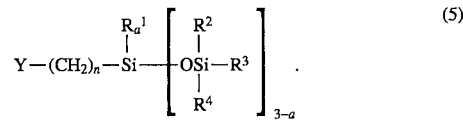

This compound possesses similar characteristics, especially a boiling point, to those of the compound (1) of the intended product of this invention. Therefore distillation of the product mixture will not separate them and the compound (5) will remain in the final product as an impurity.

On the other hand, a larger molar ratio than the 1/(2-a) level will lower the yield by leaving unreacted the portion of the compound (4), in which b is 2 or 3. Further, the unreacted portion of the compound will produce multiple numbers of silanol groups at the next reaction stage, hydrolysis. These silanol groups will have a lower stearic hindrance, therefore, they will condense to form oil-like or gel-like products. This will also reduce the yield.

It is also obvious that the contamination of water must be avoided in the reaction expressed by (B). For example, the silanols expressed by the formula (4) may produce water during storage by condensation as in reaction (A). The water produced by such condensation will react with the Si-X bond in the organohalosilane, expressed by the formula (2).

Therefore it will disturb the molar ratio balance of compounds (2) and (3) within the reaction system and cause a lowering in yield. Therefore it is desirable to perform a dehydration treatment by using anhydrous sodium sulfate, anhydrous magnesium sulfate, anhydrous potassium chloride, silica gel, or molecular sieves, and more preferably a further distillation for purification, prior to the use of the silanols expressed by the formula (3). It is also desirable to ventilate the inside of the reaction vessel with dry nitrogen gas, or to dehydrate reaction reagents prior to the use, for the same reason.

On the other hand, the silanol group within the compounds of this invention, expressed by the chemical formula (1), are restricted from condensation with each other due to the stearic hindrance. Therefore, the compounds of formula (1) are stable towards heating associated with, for example, distillation. This indicates that the bulkier the groups of $R^1$, $R^2$, $R^3$, $R^4$, and $Y-(CH_2)_n$ in the said compound (1) of this invention, the better is the stability in the protection towards condensation. Based on the above, organochlorosilanes which are easily accessible and easily handled are desirably used as the organohalosilane expressed by the formula (2) in this invention.

Examples of such organochlorosilanes are: ethyl trichlorosilane, phenyl trichlorosilane, vinyl trichlorosilane, n-hexyl trichlorosilane, n-octyl trichlorosilane, n-decyl trichlorosilane, n-dodecyl trichlorosilane, 3-(meth) acryloyloxy propyl trichlorosilane, 3-[2-(meth) acryloyloxy ethoxy] propyl trichlorosilane, 11-(meth) acryloyloxy undecyl trichlorosilane, allyl trichlorosilane, 5-hexenyl trichlorosilane, 9-decenyl trichlorosilane, chloromethyl trichlorosilane, 3-chloropropyl trichlorosilane, 3-bromopropyl trichlorosilane, 10-bromodecyl trichlorosilane, 3,3,3-trifluoropropyl trichlorosilane, 2-(nonafluorobutyl) ethyl trichlorosilane, 2-(heptadecafluorooctyl) ethyl trichlorosilane, and 2-cyanoethyl trichlorosilane; ethyl methyl dichlorosilane, phenyl methyl dichlorosilane, vinyl methyl dichlorosilane, n-hexyl methyl dichlorosilane, n-octyl methyl dichlorosilane, n-decyl methyl dichlorosilane, n-dodecyl methyl dichlorosilane, 3-(meth) acryloyloxy propyl methyl dichlorosilane, 3-[2-(meth) acryloyloxy ethoxy] propyl methyl dichlorosilane, 11-(meth) acryloyloxy undecyl methyl dichlorosilane, allyl methyl dichlorosilane, 5-hexenyl methyl dichlorosilane, 9-decenyl methyl dichlorosilane, chloromethyl methyl dichlorosilane, 3-chloropropyl methyl dichlorosilane, 3-bromopropyl methyl dichlorosilane, 10-bromodecyl methyl dichlorosilane, 3,3,3-trifluoropropyl methyl dichlorosilane, 2-(nonafluorobutyl) ethyl methyl dichlorosilane, 2-(heptadecafluorooctyl) ethyl methyl dichlorosilane, and 2-cyanoethyl methyl dichlorosilane.

As the silanols expressed by the formula (3), examples such as trimethyl silanol, dimethyl trimethyl siloxy silanol, methyl bis(trimethyl siloxy) silanol, and tris(trimethyl siloxy) silanol are particularly preferred.

The organopolysiloxane having a silanol group in this invention is a novel compound having one silanol group, which silanol group has little or no condensation, within a molecule. The selection of certain organic groups on the organopolysiloxane will even further increase its industrial value. Further, according to the manufacturing method of this invention, the organopolysiloxane having a silanol group of this invention may be manufactured easily at high purity and high yield, without requiring special instruments and techniques.

In the foregoing and in the following examples, all temperatures are set forth uncorrected in degrees Celsius; and, unless otherwise indicated, all parts and percentages are by weight. The entire disclosure of all patents cited above is hereby incorporated by reference.

EXAMPLES

Below this invention is interpreted further in detail by using Examples. However, the invention is not limited to these Examples.

EXAMPLE 1

42.4 g (0.2 mol) of 3-chloropropyl trichlorosilane, 62.6 g (0.62 mol) of triethyl amine, and 250 ml of toluene were placed within a one liter capacity flask equipped with a dropping funnel, a condenser, a thermometer, and a stirrer, and the mixture was cooled to 10° C. while stirring. Then 36.0 g (0.4 mol) of trimethyl silanol, preliminarily dehydrated, was added slowly drop by drop and the mixture was stirred at 10° C. for an hour. Further, 100 ml of 0.5 N hydrochloric acid was added and stirred at room temperature for another hour, in order to dissolve produced amine hydrochloride as well as to hydrolyze the Si-Cl bonds.

The obtained reaction mixture was separated, and the organic layer was washed with saturated salt water until neutralized. Then the solvent was eliminated by the distillation under reduced pressure after dehydration by anhydrous sodium sulfate. The obtained distillation residue was purified using a rectifying column and a colorless and transparent liquid with a boiling point of 95° to 97° C. (3 mmHg) was obtained. This liquid was tested by IR, $^1$H-NMR, and MS and identified by the elemental analysis. As a result, it was confirmed to be a compound expressed by the formula (6) below:

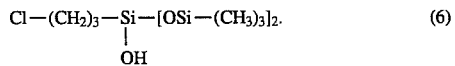

$$Cl-(CH_2)_3-\underset{\underset{OH}{|}}{Si}-[OSi-(CH_3)_3]_2. \qquad (6)$$

Figure 1:
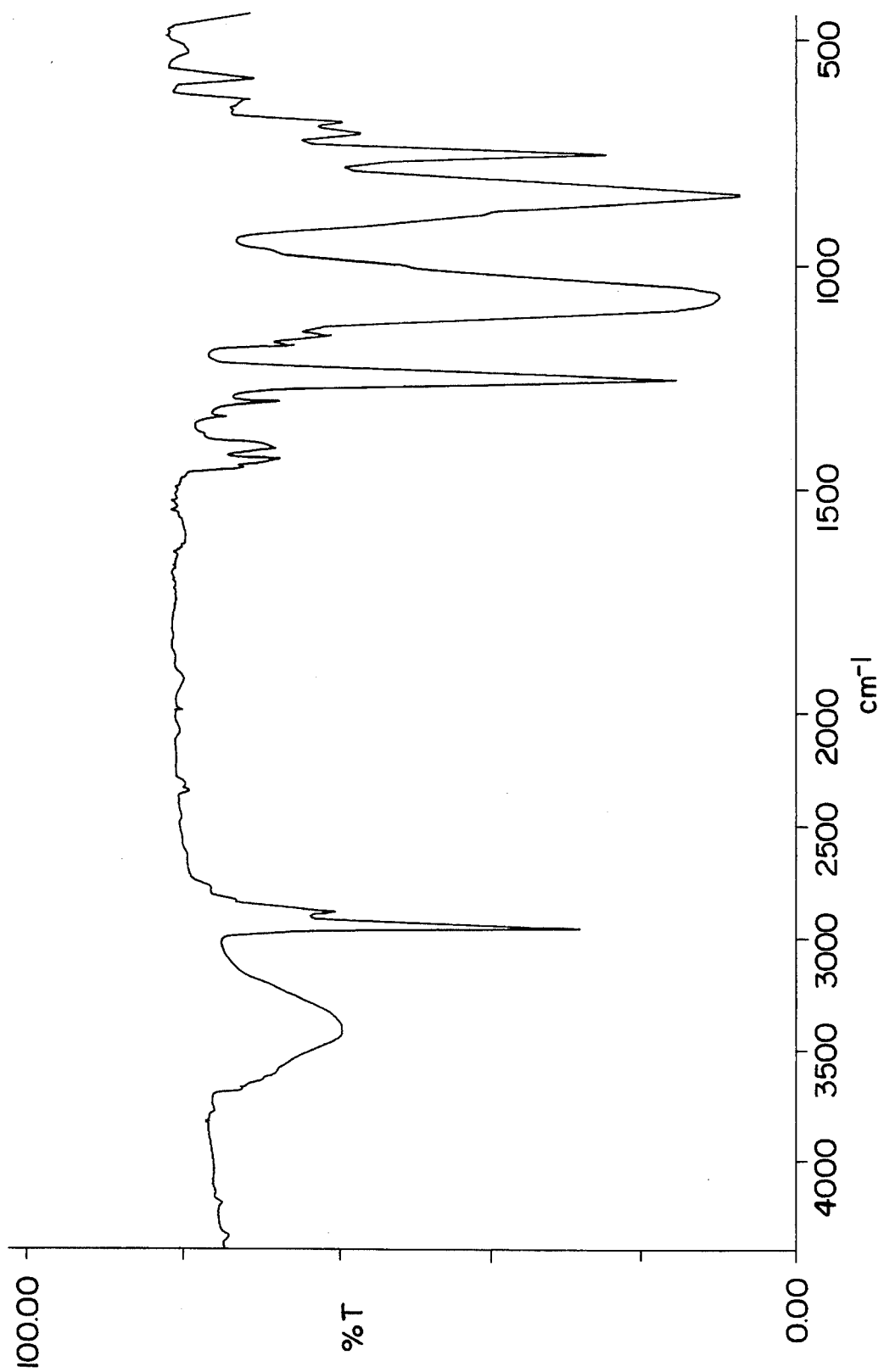
FIG. 1—IR spectrum presenting an analytical result of the organic silicone compound of Example 1.
Figure 2:
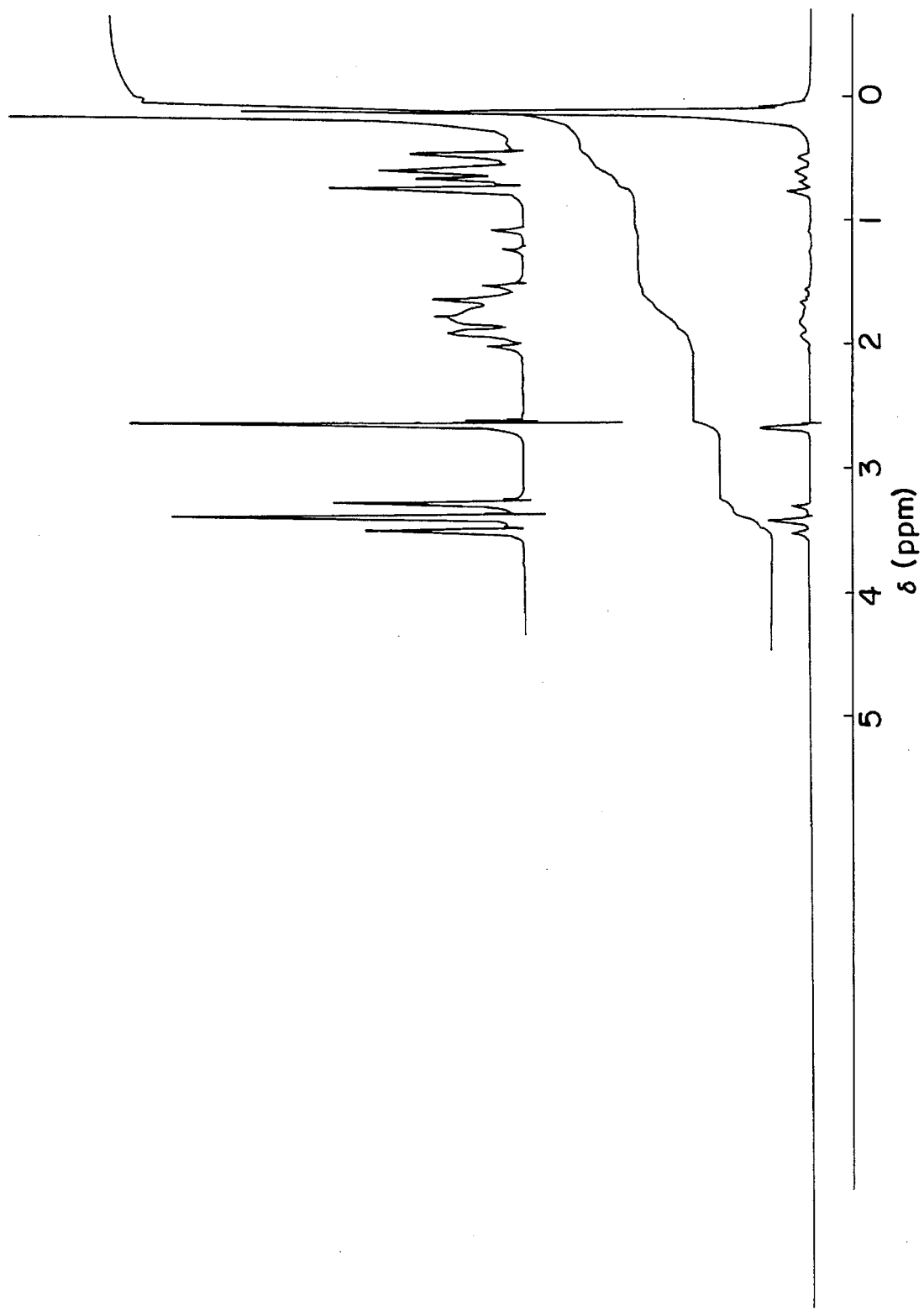
FIG. 2—$^1$H-NMR spectrum presenting an analytical result of the organic silicone compound of Example 1.

41.4 g of the compound was obtained at 68.9 % yield. The analytical results are shown below, as well as IR and $^1$H-NMR spectra in FIGS. 1 and 2, respectively.

| Analytical Results | |
|---|---|
| IR (cm$^{-1}$): | 3420 (O—H) |
| | 2960 (C—H) |
| | 1250 (Si—C) |
| | 1070 (Si—O) |
| | 710 (C—Cl) |
| $^1$H-NMR: δ (ppm) | 0.13(s, 18H, Si—CH$_3$) |
| Solvent: CCl$_4$ | 0.4–0.8(m, 2H, C—CH$_2$—Si) |
| | 1.5–2.1(m, 2H, C—CH$_2$—C) |
| | 2.7(s, 1H, Si—OH) |

| | |
|---|---|
| | 3.4(t, 2H, Cl—CH$_2$—C) |

| MS (Mass Spectroscopy): M+ (m/e): 301 | | |
|---|---|---|
| Elemental Analysis | %; | (Calculated value) |
| C | 36.11 | (35.94) |
| H | 8.29 | (8.32) |
| Cl | 11.69 | (11.81) |
| Si | 28.07 | (27.95) |

EXAMPLE 2

52.3 g (0.2 mol) of 3-methacryloyloxy propyl trichlorosilane, 62.6 g (0.62 mol) of triethyl amine, 100 mg of 2,2'-methylene bis(4-ethyl-6-tert-butyl phenol), and 250 ml of toluene were placed in the similar flask as used in Example 1. A colorless and transparent liquid with a boiling point of 97° to 100° C. (5×10$^{-3}$ Torr) was obtained by the similar method described in Example 1 including drop by drop addition of the 36.0 g (0.4 mol) of trimethyl silanol.

This liquid was tested by IR, $^1$H-NMR, and MS and identified by the elemental analysis. As a result, it was confirmed to be a compound expressed by the formula (7) below:

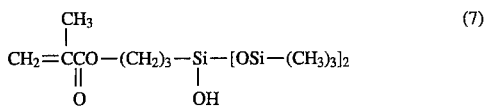

(7)

Figure 3:
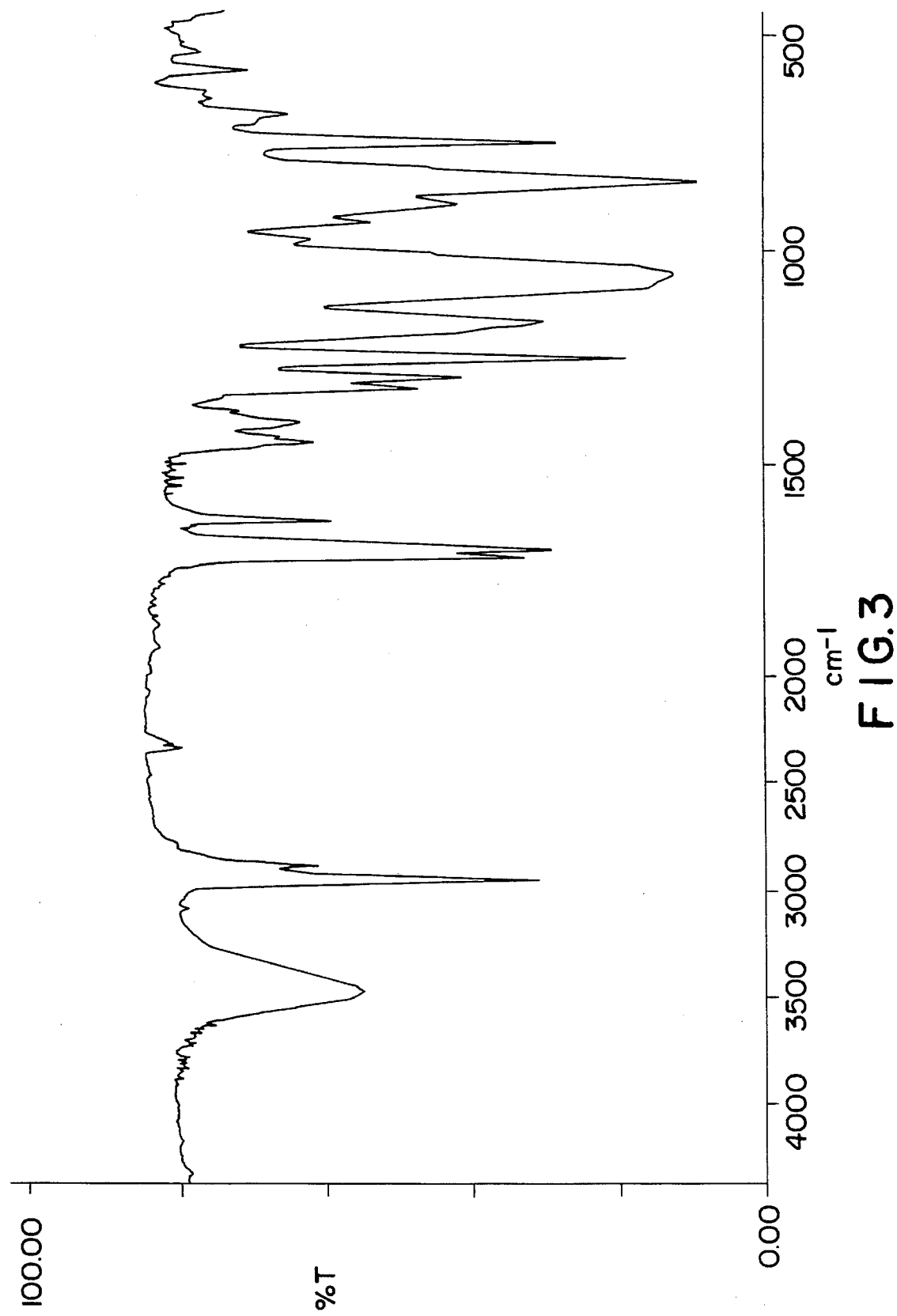
FIG. 3—IR spectrum presenting an analytical result of the organic silicone compound of Example 2.
Figure 4:
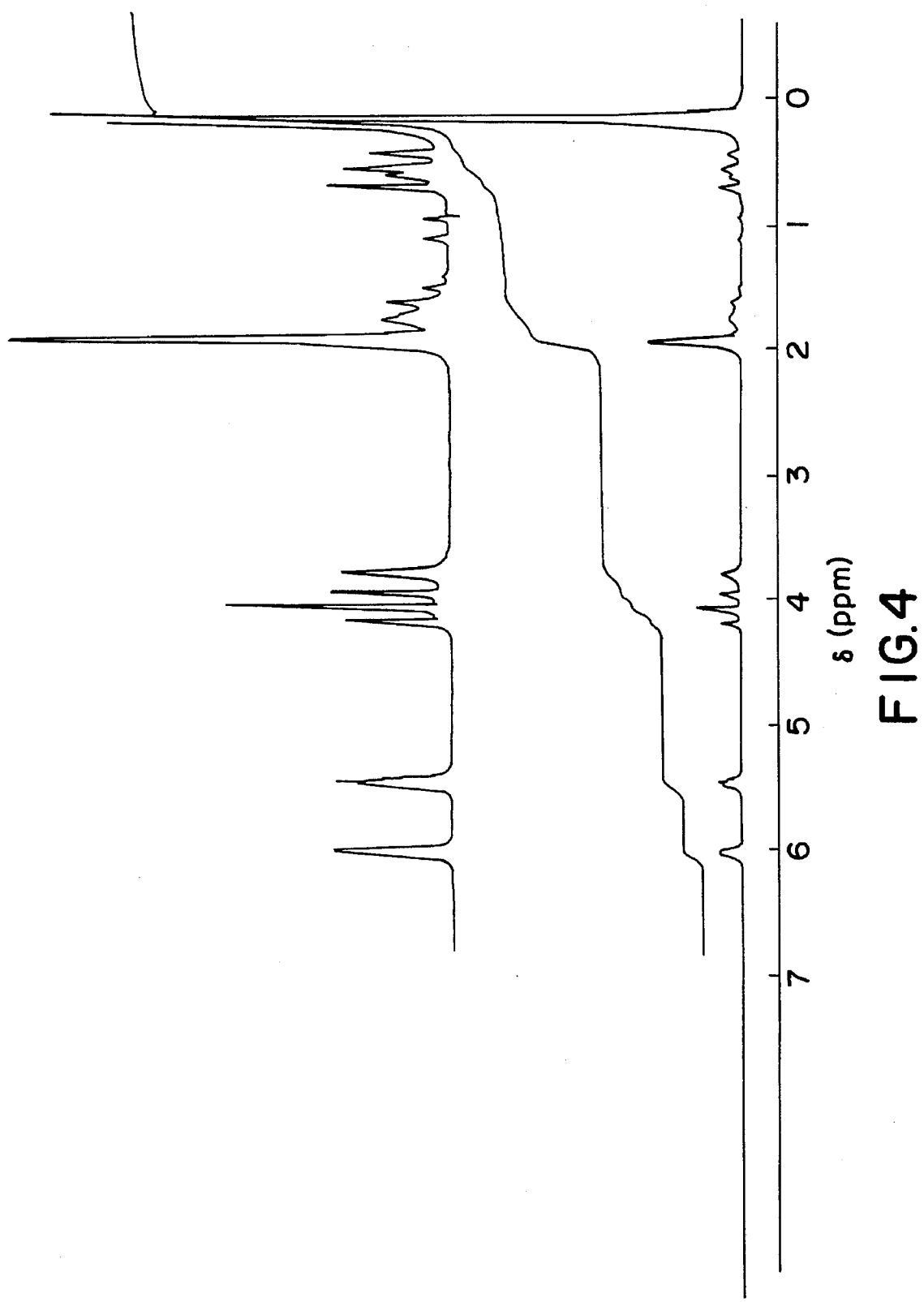
FIG. 4—$^1$H-NMR spectrum presenting an analytical result of the organic silicone compound of Example 2.

50.1 g of the compound was obtained at 71.6 % yield. The analytical results are shown below, as well as IR and H-NMR spectra in FIGS. 3 and 4, respectively.

| Analytical Results | |
|---|---|
| IR (cm$^{-1}$): | 3480 (O—H) |
| | 3090 (CH$_2$=C) |
| | 2960 (C—H) |
| | 1720, 1700 (C=O) |
| | 1250 (Si—C) |
| | 1060 (C—O, Si—O) |
| $^1$H-NMR: δ (ppm) | 0.13(s, 18H, Si—CH$_3$) |
| Solvent: CCl$_4$ | 0.4–0.8(m, 2H, C—CH$_2$—Si) |
| | 1.5–2.1(m, 5H, C—CH$_2$—C, C=C—CH$_3$) |
| | 3.8(s, 1H, Si—OH) |
| | 4.1(t, 2H, COO—CH$_2$—C) |
| | 5.4(m, 1H, H—C=C) |
| | 6.0(m, 1H, H—C=C) |

| MS (Mass Spectroscopy) M+ (m/e): 350 | | |
|---|---|---|
| Elemental Analysis | % | (Calculated value) |
| C | 44.71 | (44.57) |
| H | 8.44 | (8.57) |
| Si | 24.04 | (24.00) |

EXAMPLE 3

48.2 g (0.2 mol) of 3-methacryloyloxy propyl methyl dichlorosilane, 42.4 g (0.42 mol) of triethyl amine, 100 mg of 2,2'-methylene bis(4-ethyl-6-tert-butyl phenol), and 250 ml of toluene were placed in the similar flask as used in Example 1. A colorless and transparent liquid with a boiling point of 109° to 111° C. (2 mmHg) was obtained by the similar method described in Example 1, except that 18.0 g (0.2 mol) of trimethyl silanol was added drop by drop.

This liquid was tested by IR, $^1$H-NMR, and MS and identified by the elemental analysis. As a result, it was confirmed to be a compound expressed by the formula (8) below:

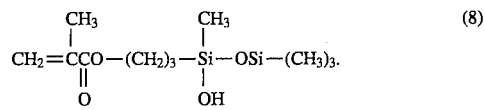

Figure 5:
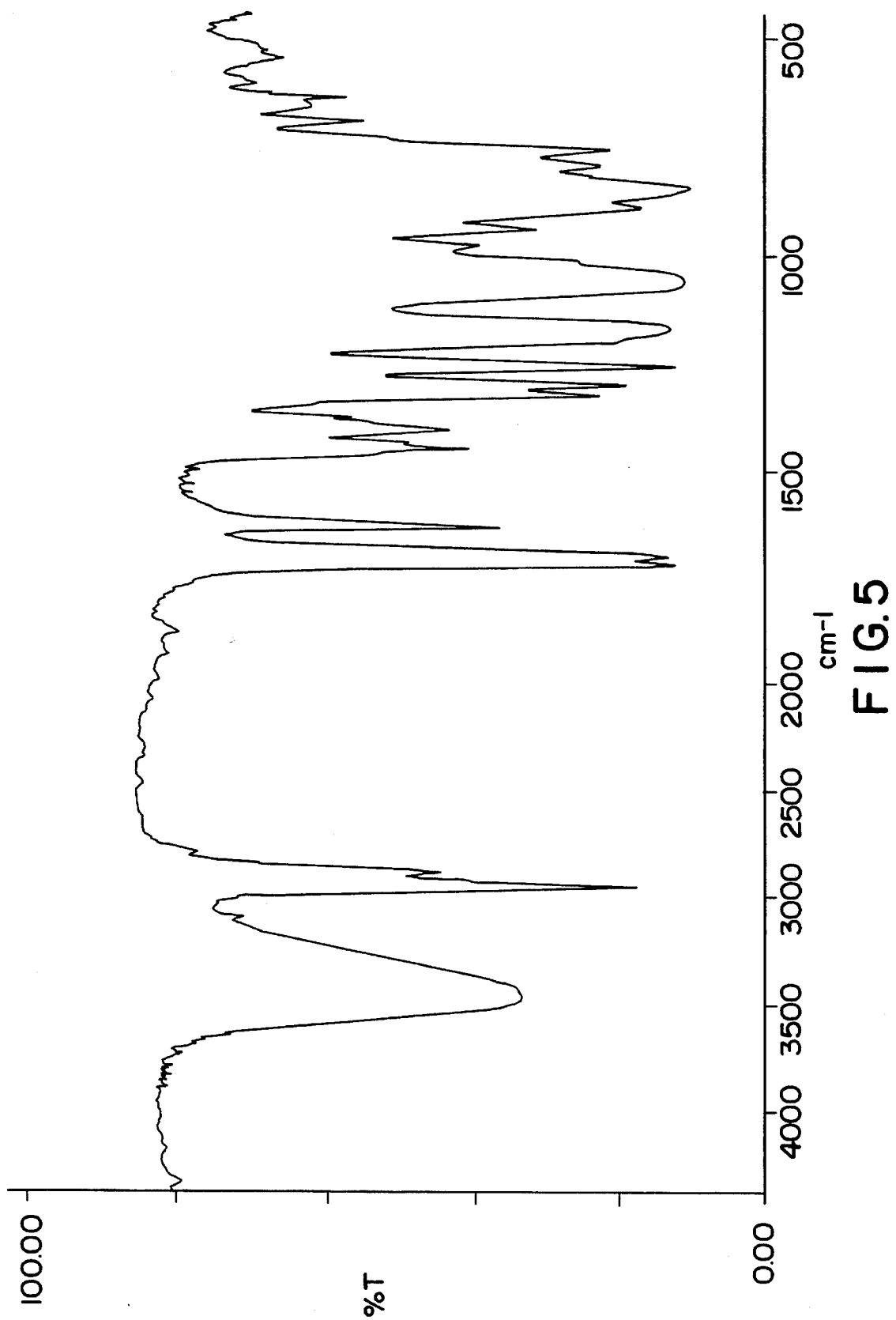
FIG. 5—IR spectrum presenting an analytical result of the organic silicone compound of Example 3.
Figure 6:
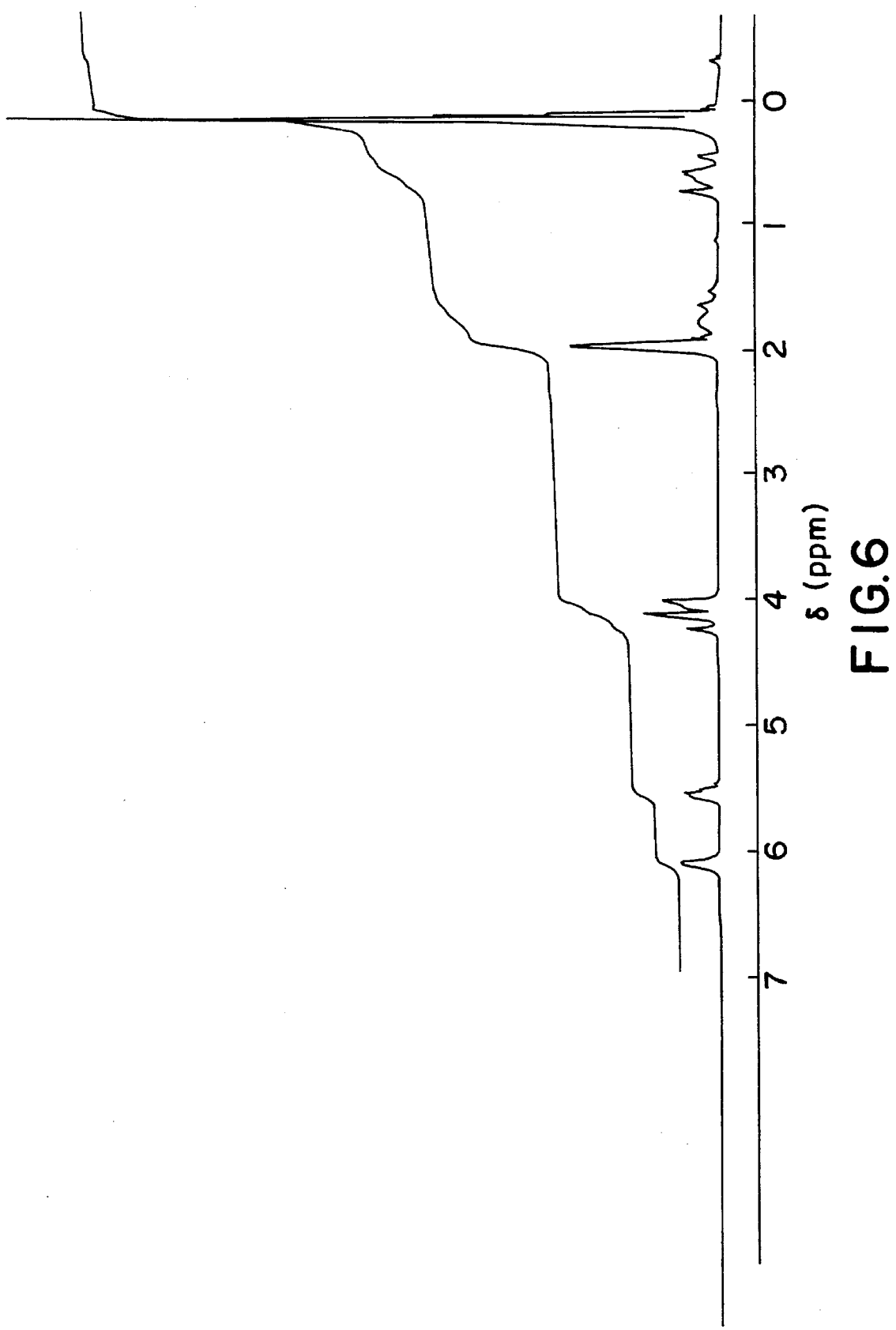
FIG. 6—$^1$H-NMR spectrum presenting an analytical result of the organic silicone compound Example 3.

32.6 g of the compound was obtained at 59.1% yield. The analytical results are shown below, as well as IR and $^1$H-NMR spectra in FIGS. 5 and 6, respectively.

| Analytical Results | |
|---|---|
| IR (cm$^{-1}$): | 3460 (O—H) |
| | 3090 (CH$_2$=C) |
| | 2960 (C—H) |
| | 1720, 1700 (C=O) |
| | 1250 (Si—C) |
| | 1060 (C—O, Si—O) |
| $^1$H-NMR: δ (ppm) | 0.10(s, 3H, C—Si—CH$_3$) |
| Solvent: CCl$_4$ | 0.13(m, 9H, O—Si—CH$_3$) |
| | 0.4–0.8(m, 2H, C—CH$_2$—Si) |
| | 1.4–2.1(m, 5H, C—CH$_2$—C, C=C—CH$_3$) |
| | 4.0–4.3(m, 3H, Si—OH, COO—CH$_2$—C) |
| | 5.5(m, 1H, H—C=C) |
| | 6.1(m, 1H, H—C=C) |

| MS (Mass Spectroscopy): M+ (m/e): 276 | | |
|---|---|---|
| Elemental Analysis | % | (Calculated value) |
| C | 47.61 | (47.83) |
| H | 8.55 | (8.70) |
| Si | 20.42 | (20.29) |

EXAMPLE 4

55.1 g (0.2 mol) of n-decyl trichlorosilane, 62.6 g (0.62 mol) of triethyl amine, and 250 ml of toluene were placed in the similar flask as used in Example 1. A colorless and transparent liquid with a boiling point of 118° to 120° C. (5×10$^{-3}$ Torr) was obtained by the similar method described in Example 1, including drop by drop addition of the 36.0 g (0.4 mol ) of trimethyl silanol.

This liquid was identified to be a compound expressed by the formula (9) below:

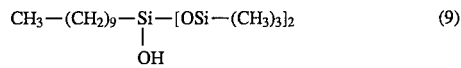

(9)

54.7 g of the compound was obtained at 75.2 % yield.

EXAMPLE 5

116.3 g (0.2 mol) of 2-(heptadecafluorooctyl) ethyl trichlorosilane, 62.6 g (0.62 mol) of triethyl amine, and 250 ml of α,α,α,α,α',α',α'-hexafluoro-m-xylene were placed in the similar flask as used in Example 1. A colorless and transparent liquid with a boiling point of 123° to 126° C. (3 mmHg) was obtained by the similar method described in Example 1, including drop by drop addition of the 36.0 g (0.4 mol) of trimethyl silanol.

This liquid was identified to be a compound expressed by the formula (10) below:

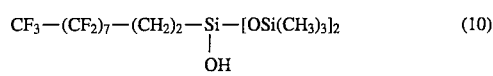

(10)

89.9 g of the compound was obtained at 67.0 % yield.

EXAMPLE 6

43.5 g (0.2 mol) of 5-hexenyl trichlorosilane, 62.6 g (0.62 mol) of triethyl amine, and 250 ml of toluene were placed in the similar flask as used in Example 1. A colorless and transparent liquid with a boiling point of 121° to 122° C. (5 mmHg) was obtained by the similar method described in Example 1, including drop by drop addition of the 36.0 g (0.4 mol) of trimethyl silanol. This liquid was identified to be a compound expressed by the formula (11) below:

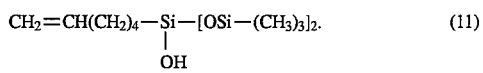
(11)

40.1 g of the compound was obtained at 65.5 % yield.

EXAMPLE 7

37.7 g (0.2 mol) of cyanoethyl trichlorosilane, 62.6 g (0.62 mol) of triethyl amine, and 250 ml of toluene was placed in the similar flask as used in Example 1. A colorless and transparent liquid with a boiling point of 134° to 135° C. (3 mmHg) was obtained by the similar method described in Example 1, including drop by drop addition of the 36.0 g (0.4 mol) of trimethyl silanol.

This liquid was identified to be a compound expressed by the formula (12) below:

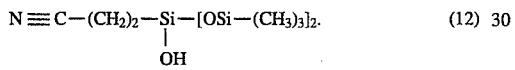
(12)

30.7 g of the compound was obtained at 55.4% yield.

Comparison Example 1

The reaction was carried out by exactly the same method described in Example 2, except that 45.0 g (0.5 mol) of trimethyl silanol was added drop by drop. As a result, the compound expressed by the formula (13) below was produced as a by-product and the purification by distillation only resulted in a mixture of the compounds (7) and (13) in a ratio of (7) to (13) of about 50:50.

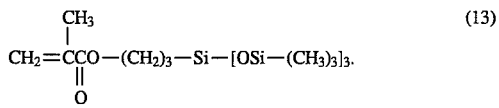
(13)

Comparison Example 2

The reaction was carried out by exactly the same method described in Example 2, except that 27.0 g (0.3 mol) of trimethyl silanol was added drop by drop. The composition expressed by the formula (7) was obtained, however, there was much residue after distillation. As a result, only 22.7 g of the product was obtained and the yield remained at 32.4%.

What is claimed is:

1. An organosiloxane having a silanol group of the formula (1) below,

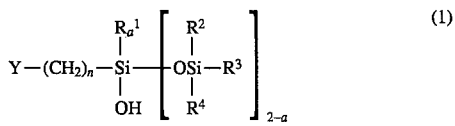
(1)

wherein $R^1$ is an unsubstituted nonvalent hydrocarbon group of 1 to 8 carbon atoms or a monovalent hydrocarbon group of 1 to 8 carbon atoms substituted by halogen or cyano groups, each of $R^2$, $R^3$, and $R^4$ is independently a monovalent hydrocarbon group of 1 to 8 carbon atoms or a siloxyl group expressed by $-OSiR^5R^6R^7$ wherein $R^5$, $R^6$, and $R^7$ are independently substituted or unsubstituted monovalent hydrocarbon groups with 1 to 8 carbon atoms, Y is a (meth)acryloyl group, n is an integer of from 0 to 12, and a is 0 or 1.

2. The organosiloxane of claim 1, wherein the monovalent hydrocarbon groups in $R^1$-$R^7$ are alkyl groups, cycloalkyl groups, alkenyl groups, a phenyl group or a benzyl group, each of which is, optionally, substituted by halogens or cyano groups.

3. The organosiloxane of claim 1, wherein at least one of $R^2$, $R^3$ and $R^4$ is a siloxyl group selected from the group consisting of trimethyl siloxyl, ethyl dimethyl siloxyl, 3,3,3-trifluoropropyl dimethyl siloxyl and cyanoethyl dimethyl siloxyl.

4. The organosiloxane of claim 1, wherein each of $R^1$, $R^2$, $R^3$ and $R^4$ is methyl.

5. An organosiloxane having a silanol group of the formula (1) below,

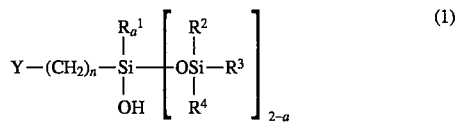
(1)

wherein $R^1$ is an unsubstituted monovalent hydrocarbon group of 1 to 8 carbon atoms or a monovalent hydrocarbon groups of 1 to 8 carbon atoms substituted by halogen or cyano groups, each of $R^2$, $R^3$, and $R^4$ is independently a monovalent hydrocarbon group of 1 to 8 carbon atoms or a siloxyl group expressed by $-OSiR^5R^6R^7$ wherein $R^5$, $R^6$, and $R^7$ are independently substituted or unsubstituted monovalent hydrocarbon groups with 1 to 8 carbon atoms provided that at least one of $r^2$, $R^3$ or $R^4$ is a siloxyl group selected from the group consisting of trimethyl siloxyl, ethyldimethyl siloxyl, 3,3,3,-trifluoropropyl dimethyl siloxyl and cyanoethyldimethyl siloxy, Y is either a hydrogen atom, a halogen atom, or a monovalent organic group of 1 to 12 carbon atoms, n is an integer of from 0 to 12, and a is either 0 or 1, with the proviso that the grouping, Y—(CH$_2$)$_n$—Si is not H-Si, CH-Si or a hydrolyzable silyl group.

6. The organosiloxane of claim 5, wherein the monovalent hydrocarbon groups in $R^1$-$R^7$, which are not siloxyl groups, are alkyl groups, cycloalkyl groups, alkenyl groups, a phenyl group or a benzyl group, each of which is, optionally, substituted by halogens or cyano groups.

7. The organosiloxane of claim 5, wherein Y is an alkenyl group, an alkynyl group, a (meth)acryloyl group, a cyano group or a nitro group.

8. The organosiloxane of claim 5, wherein Y is a (meth)acryloyl group, a vinyl group, a halogen-substituted hydrocarbon group or a cyano group.

9. The organosiloxane of claim 5, wherein Y is a perfluoroalkyl group.

10. The organosiloxane of claim 5, wherein Y is a (meth)acryloyl group.

* * * * *